United States Patent
Swan et al.

(10) Patent No.: US 9,387,289 B2
(45) Date of Patent: Jul. 12, 2016

(54) INFUSION PUMP

(75) Inventors: Julian Francis Ralph Swan, Ealing-London (GB); John Danby, Witham-Essex (GB)

(73) Assignee: Danby Scientific Limited (GB)

( * ) Notice: Subject to any disclaimer, the term of this patent is extended or adjusted under 35 U.S.C. 154(b) by 0 days.

(21) Appl. No.: 12/600,124

(22) PCT Filed: May 19, 2008

(86) PCT No.: PCT/GB2008/001711
§ 371 (c)(1),
(2), (4) Date: Oct. 19, 2010

(87) PCT Pub. No.: WO2008/142394
PCT Pub. Date: Nov. 27, 2008

(65) Prior Publication Data
US 2011/0028897 A1  Feb. 3, 2011

(30) Foreign Application Priority Data
May 18, 2007 (GB) .................................. 0709580.5

(51) Int. Cl.
*A61M 1/00* (2006.01)
*A61M 5/145* (2006.01)
(Continued)

(52) U.S. Cl.
CPC .............. *A61M 5/1454* (2013.01); *A61M 5/148* (2013.01); *A61M 5/14566* (2013.01); *A61M 5/16831* (2013.01); *A61M 39/26* (2013.01); *A61M 2205/332* (2013.01); *A61M 2205/8212* (2013.01)
USPC ........................................................ 604/151

(58) Field of Classification Search
CPC ............ A61M 5/1456; A61M 5/1454; A61M 5/14566; A61M 2005/14506; A61M 2005/2073; A61M 2005/202; A61M 5/172; A61M 2005/3151; A61M 5/142; A61M 5/2053; A61M 5/282; A61M 5/31583; A61M 5/31586; A61M 5/482; Y10S 128/12; B67D 1/0079; B67D 1/102; F04B 2201/12
USPC ........................................................ 604/151
See application file for complete search history.

(56) References Cited

U.S. PATENT DOCUMENTS 4,313,439 A   2/1982 Babb et al.
4,668,220 A * 5/1987 Hawrylenko ................. 604/155
(Continued)

FOREIGN PATENT DOCUMENTS

DE   19713082   10/1998
GB   2166497    5/1986
(Continued)

OTHER PUBLICATIONS

International Search Report and Written Opinion for PCT/GB2008/001711 dated Nov. 11, 2008.

*Primary Examiner* — Jason Flick
(74) *Attorney, Agent, or Firm* — Holland & Hart, LLP (57) ABSTRACT

An infusion pump for administering controlled doses of a fluid comprises: a receptacle (2) for storing the fluid (6), the receptacle having an outlet (8) for dispensing the fluid; a plunger (12); a propulsion mechanism (14) which urges the plunger (12) in a direction to pressurise the fluid (6) and dispense it through the outlet (8); and a retaining member (16) which acts on the plunger (12) to control or prevent travel of the plunger (12); characterised in that the retaining member (16) is operably connected to a stepper motor (24) via a worm (22) and worm-wheel (18) drive.

22 Claims, 5 Drawing Sheets (51) Int. Cl.
*A61M 5/148* (2006.01)
*A61M 5/168* (2006.01)
*A61M 39/26* (2006.01)

(56) References Cited

U.S. PATENT DOCUMENTS

| | | | |
|---|---|---|---|
| 5,034,004 A * | 7/1991 | Crankshaw | 604/154 |
| 6,413,238 B1 * | 7/2002 | Maget | 604/132 |
| 2003/0149402 A1 * | 8/2003 | Gerlach et al. | 604/151 |
| 2004/0116847 A1 * | 6/2004 | Wall | 604/93.01 |
| 2005/0277912 A1 * | 12/2005 | John | 604/890.1 |
| 2010/0174182 A1 * | 7/2010 | Costanzo | 600/431 |

FOREIGN PATENT DOCUMENTS

| | | |
|---|---|---|
| GB | 2166497 | 5/1986 |
| JP | 2002078799 A | 3/2002 |
| JP | 2005538773 A | 12/2005 |
| WO | 2004/024211 A2 | 3/2004 |
| WO | 2004024218 | 3/2004 |

* cited by examiner

INFUSION PUMP

BACKGROUND a. Field of the Invention

The present invention relates to an infusion pump for administering controlled doses of a fluid, notably to an ambulatory infusion pump for administering fluid medicament to a patient.

It can be advantageous to provide a patient with small doses of a medicament over a long period of time, rather than administering a comparatively large dose by a single injection. For example, medicaments such as insulin for diabetics are more effective when administered in this manner, and particularly if the dosage can be adjusted automatically in response to changes in blood glucose levels. An ambulatory infusion pump is worn by a patient and can provide for such an improved dosing regime.

b. Related Art

WO 2004/024218 describes an infusion pump comprising a reservoir for storing a liquid agent, and a drive mechanism for propelling a piston towards an outlet from the reservoir in order to discharge the agent. The drive mechanism permanently forces the piston forwards, and a locking mechanism is provided for permanent locking of progress of the piston. The locking mechanism is released by operation of an escapement mechanism under electronic control for discharge of the agent.

SUMMARY OF THE INVENTION

According to a first aspect of the present invention there is provided an infusion pump for administering controlled doses of a fluid, the pump comprising:
- a receptacle for storing the fluid, the receptacle having an outlet for dispensing the fluid;
- a plunger;
- a propulsion mechanism which urges the plunger in a direction to pressurise the fluid and dispense it through the outlet; and
- a retaining member which acts on the plunger to control or prevent travel of the plunger;
- characterised in that the retaining member is operably connected to a stepper motor via a worm and worm-wheel drive.

By using a worm and worm-wheel driven by a stepper motor, it is possible to exercise greater control over the rate at which the plunger travels and hence improve the accuracy of dose control when administering a fluid from the pump. By contrast to known infusion pumps, the worm-wheel drive of the present invention does not have a set stroke but instead can be used to accurately control, and change as required, the rate at which the retaining member extends from the wheel, thereby directly effecting the rate at which fluid is expelled from the syringe.

In a preferred arrangement, the plunger pressurises the fluid by means of a piston which is located in the receptacle in contact, directly or indirectly, with the fluid.

The plunger may itself comprise a piston, or alternatively, the piston may be secured to the plunger, for example, directly by means of an interference fit.

Accordingly, another aspect of the invention provides an infusion pump for administering controlled doses of a fluid, the pump comprising:
- a receptacle for storing the fluid, the receptacle having an outlet for dispensing the fluid;
- a piston in the receptacle;
- a propulsion mechanism which urges the piston towards the outlet to dispense the fluid; and
- a retaining member which acts on the piston to control or prevent travel of the piston towards the outlet;
- characterised in that the retaining member is operably connected to a stepper motor via a worm and worm-wheel drive.

In the present invention the angle of mating gear teeth of the worm and worm-wheel drive is preferably changed as compared to a normal worm and worm-wheel drive in which rotation of the worm would cause the wheel to turn whereas applying a torque to the wheel would normally fail to turn the worm. In other words, the gear set is normally incapable of being back-driven. In the present invention the angle of the teeth is preferably chosen to provide a gear mechanism such that the gearbox is only just not capable of being back-driven by the torque applied to the wheel axle via the retaining means ("backdrive balance"). In this way, a very small torque applied to the worm, via the motor, will advantageously allow the wheel to rotate.

When the teeth angle in the gears is selected so that the drive is close to backdrive balance, it is also possible to control the rate at which the retaining member unwinds using a very small stepper motor and very little current. The amount of torque applied to the wheel will have little effect on the torque from the worm required to allow it to turn.

This invention is particularly beneficial for an ambulatory infusion pump because it can reduce the size and weight of the pump, making it easier for the patient to wear. Also, the motor need use only a very small current, thereby providing for extended battery life and allowing the device to be worn for longer periods between recharging or replacing batteries.

The propulsion mechanism which urges the plunger or piston towards the receptacle outlet may comprise a compression spring. Alternatively, the propulsion mechanism may comprise means such as a pressurised gas to urge the plunger/piston forwards.

Conveniently, the receptacle is typically tubular, such as in the form of a syringe. In one preferred arrangement, the receptacle of the pump may comprise a collapsible container, such as an Intravenous (IV) bag with flexible walls or it may have a concertina-like structure. Advantageously, the plunger or piston pressurises the fluid by acting directly on a flexible wall of the container. It is preferred to provide the collapsible container within the receptacle because this helps protect and position it, and define an external shape. However, it is also possible that the collapsible container is itself the receptacle for the fluid, and in such a case the receptacle is defined by the walls of the collapsible container. For appearance sake or protection, or both, the pump may include external housing in which the receptacle is retained.

The retaining member may comprise any suitable means for operably attaching the plunger to the motor via the worm drive, for example a cord, chain or cable. The retaining member may be wound around the axle of the worm-wheel, which functions as a capstan or winch. Accordingly, from another aspect, the invention provides a spring-driven infusion pump in which the release of the spring is controlled by a capstan or winch.

Advantageously, the pump may further include a force detector for providing important information about the state of the pump, for example, whether the retaining member has broken or if there is an occlusion in the system. Preferably, the force detector is located on an axle of the worm-wheel.

Alternatively or in addition thereto, the pump may include an electronic controller. Usefully, the force detector may provide information specifically about the state of the retaining member (tight or slack) to an electronic controller. The pump may therefore be automated using the force detector and the electronic controller. For example, when the controller receives information from the detector that the retaining member is slack, the controller activates the stepper motor to take up the slack. Ideally, before the pump is used, the retaining member is fully wound and the stepper motor is stopped.

The pump may include one or more sensors for providing feedback to the electronic controller, for example, for sensing (measuring) the force on the wheel axle, and/or for measuring the retaining member and/or the position of the plunger or piston.

Advantageously, the electronic controller may include a boost function for inducing a rapid increase in the rate of expulsion of fluid. The controller may also limit the duration of any boost in rate according to clinical necessity. For example the controller may permit the user to press a button to cause a rapid short-term increase release of an analgesic if this does not cause the dose to exceed a harmful limit. The number and duration of such increased doses may be measured and limited by the controller to prevent a user overdosing.

By providing electronic control of the infusion pump, the flow rate of the fluid to the patient may be modified against a time base or modified by other influences such as user input (for example, to enable PCA—Patient Controlled Analgesia) or external equipment, which monitors the patient's vital signs. Electronically controlling the pump has other advantages such as providing dosing programs to predetermine the rate the fluid is dispensed from the receptacle for a specific duration.

It is desirable to provide the pump with a hydraulic lock to prevent egress of fluid from the outlet before the pump is in use. Thus, in a preferred embodiment the outlet of the receptacle is provided with a screw thread for fitting into a cap having a mating-screw thread. Usefully, the outlet is further provided with a valve member which will only permit fluid flow when it is inwardly displaced, for example, a luer-activated valve.

The pump according to the invention is preferably provided with a brake mechanism to slow or stop the plunger from moving uncontrollably, for example, in the event the retaining member breaks.

For example, the plunger (or piston) may comprise a brake member in the form of a cruciform spring. Desirably, in normal operation of the pump, the cruciform spring adopts a retracted configuration in which it does not engage with a wall of the receptacle. Usefully, the plunger/piston is free to travel within the receptacle when the retaining means permits the propulsion mechanism to move the plunger.

However, if the retaining means breaks, the cruciform spring adopts a substantially planar configuration and engages with the wall of the receptacle. Advantageously the engagement between the cruciform spring and the wall induces a braking effect which stops or hinders the movement of the piston.

The Applicant envisages that other braking mechanisms may be provided; for example the plunger may be caused to tilt if the retaining member breaks, causing jamming between the plunger or the piston and the receptacle wall. Preferably, the brake mechanism is self-activating. More preferably, the greater the force urging the plunger to pressurise the liquid, the greater that force urges the brake to be deployed.

Accordingly another aspect of the invention comprises an infusion pump for administering controlled doses of a fluid, the pump comprising:

a receptacle for storing the fluid, the receptacle having an outlet for dispensing the fluid;
a plunger in the receptacle;
a propulsion mechanism which urges the plunger towards the outlet to dispense the fluid; and
a retaining member, optionally under electronic control, which acts on the plunger to control or prevent travel of the plunger towards the outlet;
characterised in that the plunger includes a brake member which is adjustable between an active position in which it prevents or inhibits relative movement between the plunger and the outlet, and a passive position in which it does not prevent or inhibit movement; wherein the brake member is held in the passive position by the retaining member in normal operation but is released to adopt the active position if the retaining member fails.

It will be appreciated that the drive mechanism may be sold as part of the pump or it may be manufactured and sold separately. A further aspect of the invention therefore embraces a drive mechanism for an infusion pump for administering controlled doses of a fluid, the drive mechanism comprising:

a plunger;
a propulsion mechanism which urges the plunger in a predetermined direction; and
a retaining member which acts on the plunger to control or prevent travel of the plunger;
characterised in that the retaining member is operably connected to a stepper motor via a worm and worm-wheel drive.

BRIEF DESCRIPTION OF THE DRAWINGS

The invention will now be further described, by way of example only, with reference to the following drawings in which.

DETAILED DESCRIPTION

Figure 1:
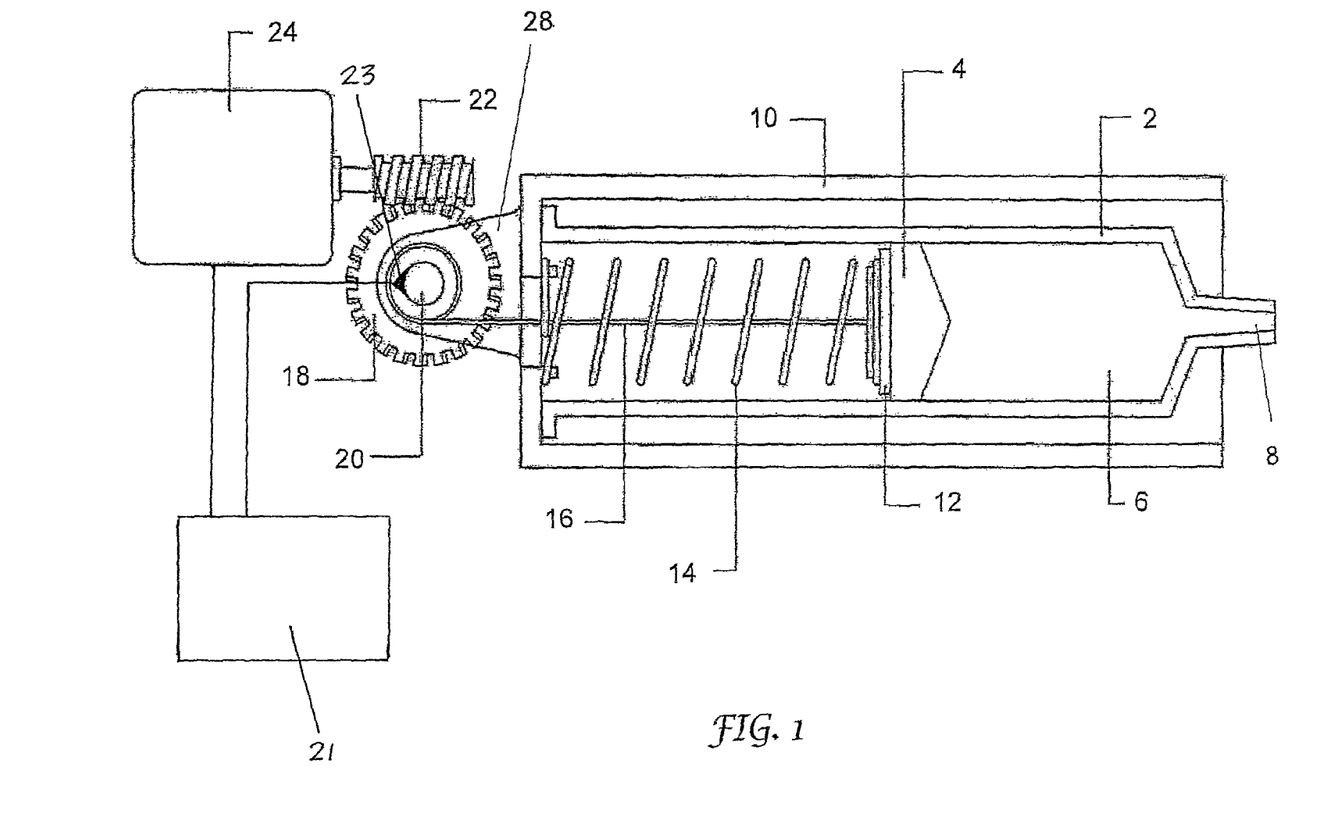
FIG. 1 is a part sectional view of a first embodiment of an infusion pump in accordance with an aspect of the invention.

The infusion pump shown in FIG. 1 comprises a housing 10 in which is mounted a receptacle 2, in this example a syringe, for storing a liquid infusate 6. The syringe 2 has an outlet nozzle 8 for dispensing the liquid 6. A propulsion mechanism, in this example a compression spring 14, acts on a plunger 12 to urge a piston 4 towards the outlet nozzle 8 to dispense the liquid 6. One end of the spring 14 is fixed to the housing 10, and the other end is fixed to the plunger 12. Unless restrained, the force of the spring 14 will drive the piston 4 all the way down the syringe 2 until it fully expels the liquid 6 and abuts the exit nozzle 8.

To control the rate of movement of the piston 4, it is engaged by a retaining member 16, in this example a cord or cable, for example having a spool diameter of approximately 8 mm. The cord 16 is wound around an axle 20 of a worm-wheel 18 mounted to the housing 10 by a bracket 28, the axle 20 functioning as a capstan. The worm-wheel is turned by a worm 22 powered by a stepper motor 24.

To understand the invention fully, it is worth considering typical worm gear arrangements. In most worm gear arrangements rotating the worm will cause the wheel to turn whereas applying a torque to the wheel will fail to turn the worm. In other words the gear set is incapable of being back-driven. It is understood that the angle of the mating gear teeth is responsible for this effect. If this angle is changed, the effect may be reduced or enhanced. The angle of the teeth in the mating gears 18, 22 of the present invention is chosen relative to a normal angle, for example it may be changed by approximately 2.32 degrees, to provide a gear mechanism such that the gearbox is only just not capable of being back-driven by the torque applied to the axle 20 via the cord 16 and spring 14 ("backdrive balance"). Therefore a very small torque applied to the worm 22, for example in the range of 1.75 to 3.00 mNm, via the motor 24, will allow the axle 20 to rotate. Thus it is possible to control the rate at which the axle is allowed to unwind using a very small motor 24, using very little current. If the gearbox is on the point of backdrive balance the amount of torque applied to the axle 20 will have little effect on the torque from the worm 22 required to allow it to turn. In practice, however, it is necessary to provide a safety margin in order to prevent uncontrolled rotation of the axle 20 under low friction conditions or in response to external knocks or accelerations. This is accomplished by calculating the tooth angle at backdrive balance and then slightly reducing that angle with respect to the normal.

The motive force needed to infuse liquid infusate 6 into a patient is supplied by the operator (patient, clinician, doctor, carer, etc) compressing the spring 14 by loading a filled syringe 2 into the housing 10. The filled, or partly filled, syringe 2 has a primed patient connection tube (not shown) attached to the nozzle 8 prior to insertion into the housing, and this tube will be occluded to prevent flow by the use of a releasable seal such as a slide clamp or similar device. The sealed tube provides a hydraulic lock which enables the insertion of the full syringe. Inserting the syringe will cause the piston 4 to push the plunger 12 away from nozzle 8, compressing the spring 14 and causing the cord 16 to lose tension. A force detector 23 on the axle 20 will provide information about the state of the cord 16 (tight or slack) to an electronic controller 21, and when the controller detects that the cord is slack the stepper motor 24 is started up to take up the slack, stopping when the cord 16 is fully wound on the axle 2. The infusion pump is then ready for use once the patient connection tube has been unclamped. The worm hear arrangement allows the stepper motor to control the rate at which the cord 16 is allowed to extend from the axle 20, thus allowing the spring 14 to drive the plunger 12, and in turn the syringe piston 4, into the infusate 6 contained in the syringe 2 and therefore into the patient.

The use of a force detector on the axle 20 also provides important information about the state of the infusion, for example whether the cord 16 has broken or if there is an occlusion in the system.

Figure 4:
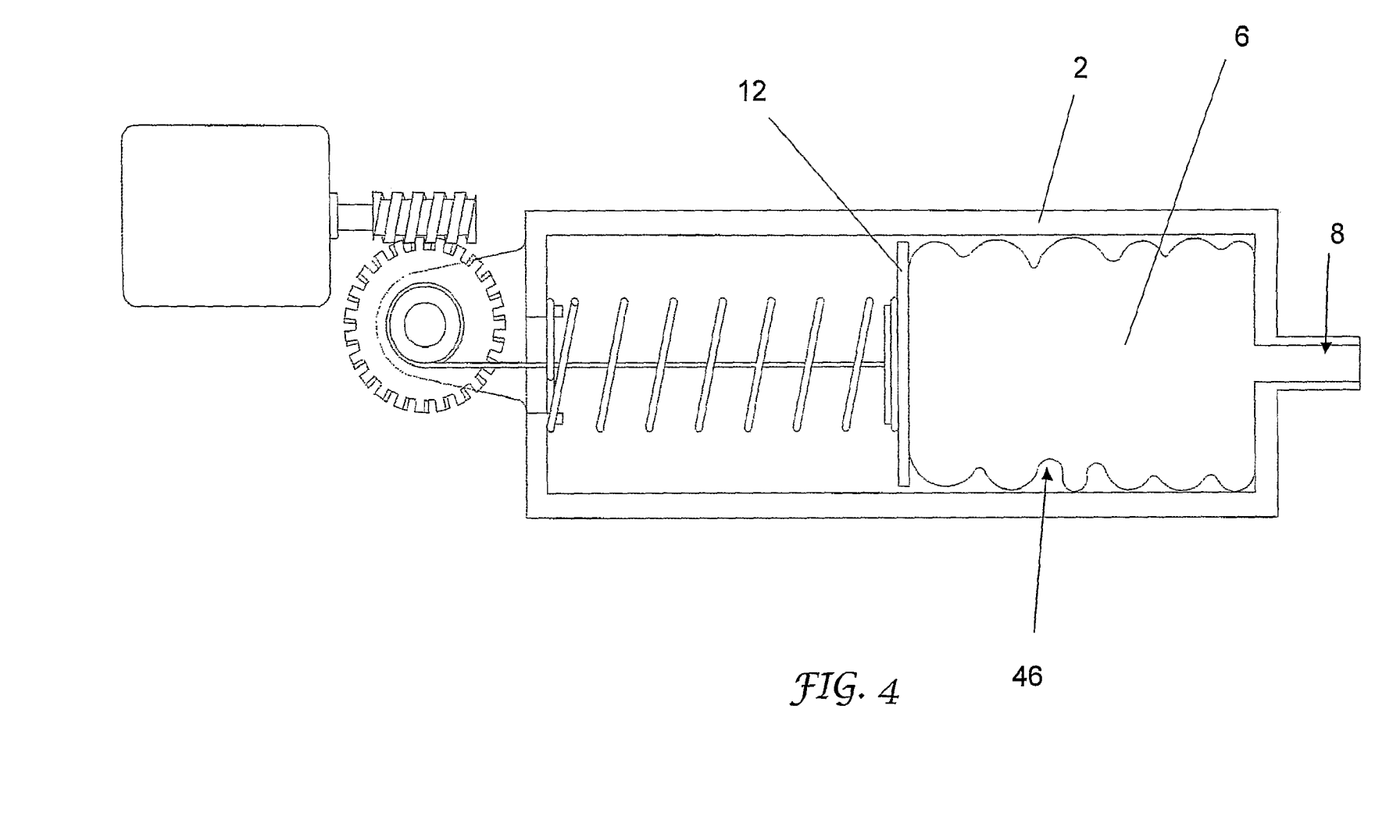
FIG. 4 is a part sectional view of a further embodiment of an infusion pump in accordance with an aspect of the invention.

Turning now to FIG. 4, another embodiment of the invention is shown, in which the infusate 6 is contained within a collapsible container 46. The collapsible container 46 may be an IV bag with flexible walls, as illustrated here, or may have a concertina-like structure. Instead of acting via a piston, the plunger 12 pressurises the infusate 6 by acting directly on a wall of the container 46. Although it is preferred to provide the collapsible container within the receptacle 2, because this helps protect and position it, and define an external shape. It would also be possible to use the collapsible container 46 as the only receptacle for the infusate 6 and in this case the receptacle would be defined by the walls of the collapsible container 46.

If the cord 16 breaks, this will permit the spring 14 to drive the piston 4 fully towards the nozzle 8, as described earlier, which could endanger the health of the patient by providing too high a dose of medicament. Accordingly, it is desirable to provide a brake mechanism to slow or stop the piston in the event of cord failure. A suitable brake mechanism is illustrated in the embodiment shown in FIGS. 2 and 3.

Figure 2:
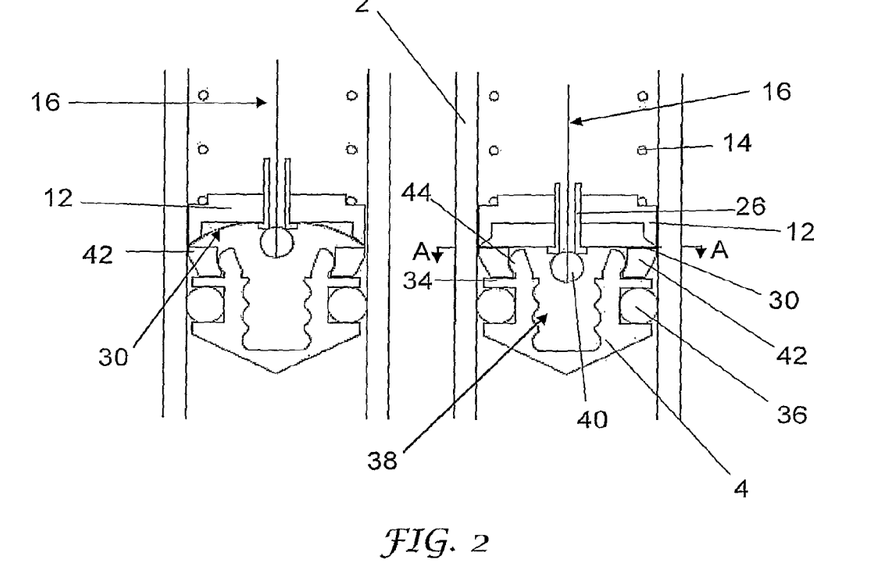
FIG. 2 is a sectional view of another embodiment of an infusion pump in accordance with an aspect of the invention.
Figure 3:
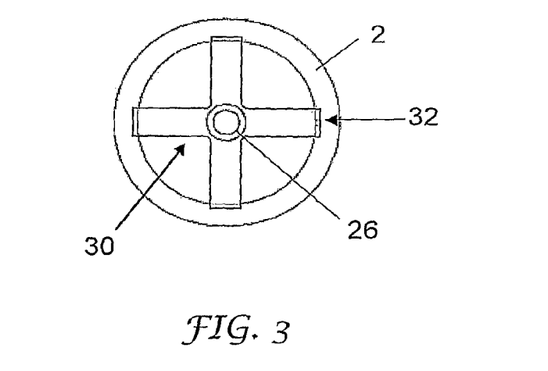
FIG. 3 is a sectional view along the line A-A of FIG. 2.

In this embodiment, an 'o'-ring 36 disposed around the piston 4 provides a seal; however it will be understood that the sealing function could be provided by the piston itself if formed from a suitable compliant material. The piston 4 has a hollow inner threaded portion 38, which receives a syringe handle (not shown) when the syringe 2 is initially filled with liquid. The handle is then removed and the syringe can be inserted into the housing 10.

The spring 14 acts on a plunger 12 having a central hole in which is fitted a flanged tube 26. The cord 16 is disposed through the tube 26 and retained by a stopper 40. The plunger 12 has a downwardly and inwardly directed collar 42 which locates on an annular projection 34 on the piston 4. The collar 42 is an interference fit for the neck 44 of the piston 4 so that when the two are pushed together the plunger 12 positively locks to the piston 4. This provides an anti-syphon feature which inhibits the piston 4 from travelling away from the plunger 12 if negative pressure is present at the nozzle end.

A brake member 30, in this example a cruciform spring, is disposed between the upper part of the plunger 12 and the flange of the tube 26. The collar 42 has openings in which are received the tips of the arms 32 of the cruciform spring 30. When the cord 16 is under tension, as illustrated in the left hand drawing of FIG. 2, the centre of the cruciform spring 30 is lifted relative to the arms 32 so that the spring 30 adopts a retracted configuration in which it does not engage with the wall of the syringe 2. In normal operation the cruciform spring 30 is maintained in this retracted configuration and the piston 4 is free to travel within the syringe 2 when the cord 16 permits the spring 14 to move the piston.

If the cord 16 fails, for example if it breaks, as illustrated in the right hand side drawing of FIG. 2, the cruciform spring 30 is free to adopt a rest configuration in which it is substantially planar and in which the tips of the arms 32 engage with the wall of the syringe 2, as illustrated in FIG. 3. This engagement provides a braking effect which stops or hinders relative movement between the piston 4 and the nozzle 8. In this embodiment, the force of the spring 14, via the plunger 12, urges the cruciform spring 30 to change from the retracted configuration to the rest configuration. This arrangement provides a self-activating feature for the brake, whereby the greater the spring force urging the plunger to pressurise the liquid, the greater that force urges the brake 30 to be deployed.

Figure 6:
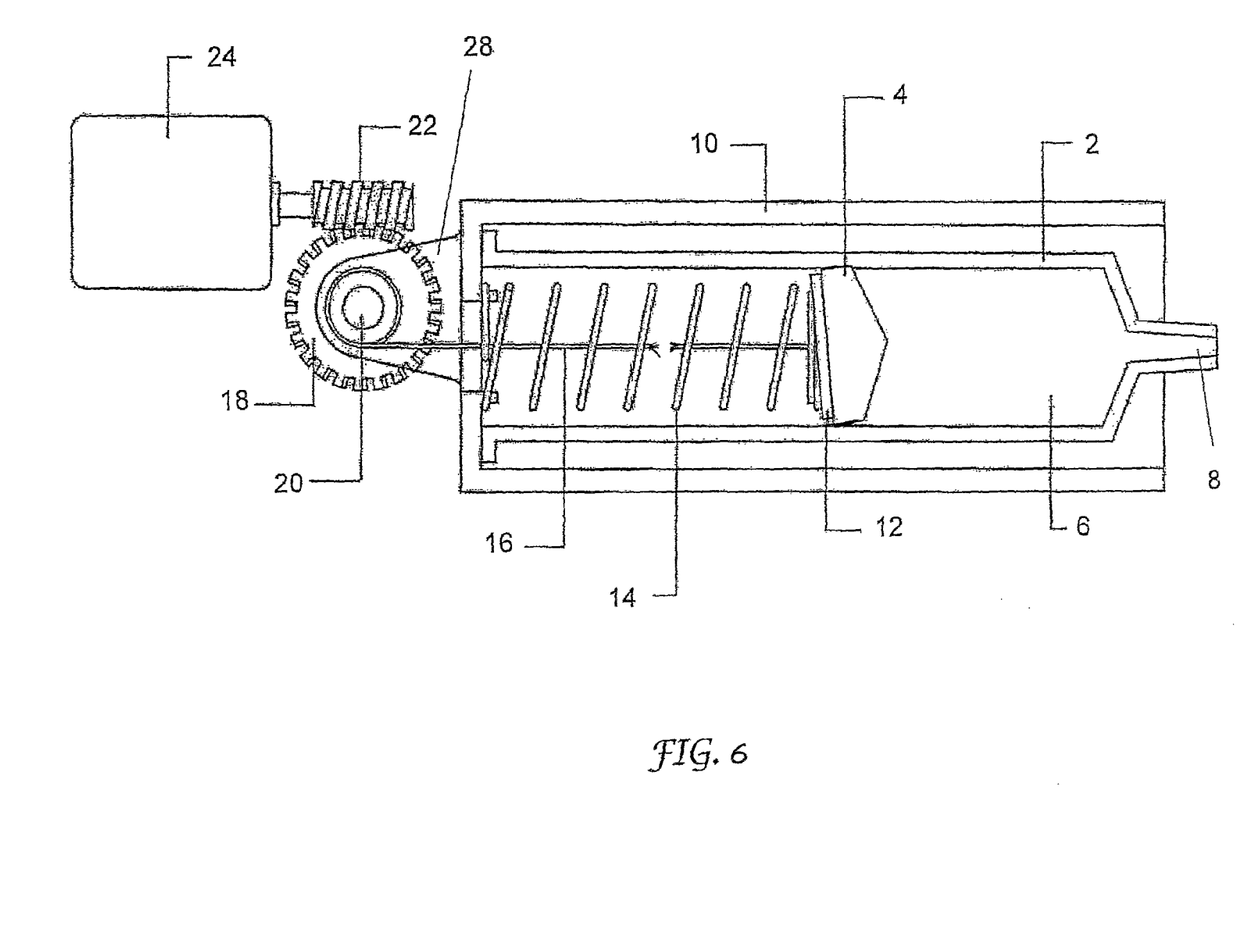

It will be understood that other brake mechanisms may be provided; for example as shown in FIG. 6, the plunger 12 may be caused to tilt if the cord 16 fails, causing jamming between the plunger 12 or the piston 4 and the syringe wall 2.

By providing electronic control of the infusion pump it can be made capable of accepting a complex programme in which the flow rate may be modified against a time base or modified by other influences such as user input (i.e. PCA—Patient Controlled Analgesia) or a patient's vital signs. The electronic control system may be provided with feedback from sensors. In addition to measuring the force on the axle 20, sensors may measure the cable and/or the position of the plunger or piston.

Before a syringe is loaded in the housing, the controller may be in an OFF or standby mode, with the force detector on the axle active. When the syringe is inserted in the housing, this is detected by the force detector causing the controller to switch to an ON or active state, or causing the system to 'boot up'. This arrangement helps conserve battery use while providing rapid and failsafe response when a user inserts a syringe.

Figure 5A:
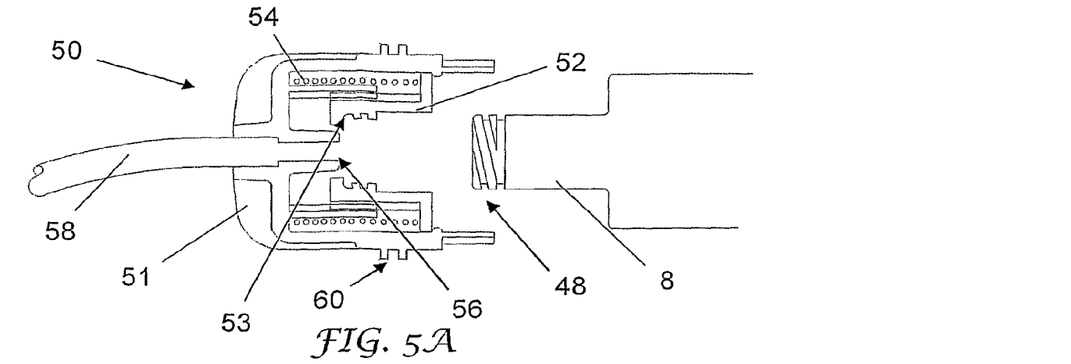
FIGS. 5a, 5b and 5c each show a sectional view through a part of a device in accordance with a further aspect of the invention; and, FIG. 6 is a part sectional view of an infusion pump with a plunger caused to tilt.

As previously discussed, it is desirable to provide the device with a hydraulic lock to prevent egress of fluid from the outlet 8 until the system has been primed by inserting the full syringe into the housing 10 against the force of the spring 14. One convenient way of achieving this is by means of a Luer-activated device, as shown schematically in FIG. 5. Here, the outlet 8 is provided with a screw thread 48, for fitting into a cap 50 which has a complementary internal screw thread 53. The cap 50 comprises an inner cap member 52, which carries the screw thread 53, and an outer cap member 51. The cap members 51, 52 are axially slideable relative to one another with a cap spring 54 urging them into an extended configuration. A central projecting tube ('Luer') 56 is fluidly connected to a patient connection tube 58 in a manner known per se. Within the outlet 8 is located a spring-biased valve member 66 (shown schematically in FIG. 5C). The valve member 66 normally prevents fluid egress from the outlet 8 but permits fluid flow when inwardly displaced.

Figure 5B:
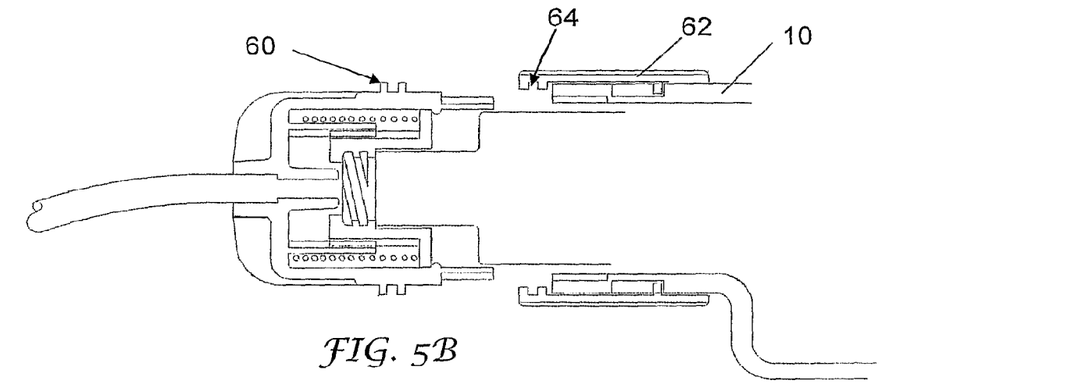
Figure 5C:
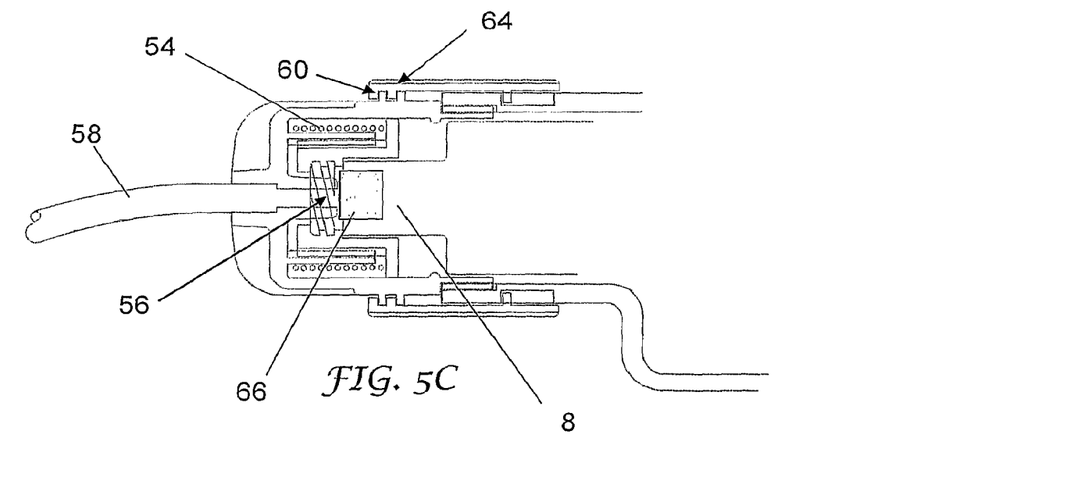

To fit the cap 50 to the outlet 8, the outlet 8 is inserted into the cap 50 and rotated to inter-engage the screw threads 48, 53 (FIG. 5B). The cap 50 is fitted to the outlet 8 but fluid cannot pass between them because the valve member 66 is not displaced. The housing 10 is provided with a locking sleeve 62 which is slidable and rotatable relative to the housing 10 and which carries a sleeve screw thread 64 which is complementary to a cap screw thread. To permit fluid flow, the locking sleeve 62 is slid up the outlet 8 to a point at which the screw threads 60, 64 can inter-engage. This movement causes the outlet 8 and inner cap member 52 to slide farther into the outer cap member 51 so that the luer 56 is inserted into the outlet 8 and displaces the valve member 66, thereby creating a fluid connection between the infusate 6 and the patient connection tube 58. Inter-engagement of the screw threads 60, 64 secures the cap and outlet together in this fluid-flow state. To recreate the hydraulic lock condition, the screw threads 60, 64 are disengaged, permitting the cap spring 54 to push the inner cap 52 and outlet 8 away from the luer 56.

It is appreciated that features of the invention, which are, for clarity, described in the context of separate embodiments, may also be provided in combination in a single embodiment. Conversely, various features of the invention which are, for brevity, described in the context of a single embodiment, may also be provided separately, or in any suitable combination.

The invention claimed is:

1. An infusion pump for administering controlled doses of a fluid, the pump comprising:
   a receptacle for storing the fluid, the receptacle having an outlet for dispensing the fluid;
   a plunger;
   a propulsion mechanism which urges the plunger in a direction to pressurize the fluid and dispense it through the outlet;
   a retaining member which acts on the plunger to control or prevent travel of the plunger; and
   a force detector for providing information about the state of the retaining member;
   the retaining member operably connected to a motor via a worm and worm-wheel drive, in an arrangement wherein rotation of the worm causes the worm-wheel drive to rotate, and wherein the resulting rotation of the worm-wheel drive controls said travel of the plunger to dispense the fluid.

2. A pump according to claim 1, further including an electronic controller, wherein the controller receives information from the force detector to automate the pump.

3. A pump according to claim 2, wherein the electronic controller has a boost function for inducing a rapid increase in the rate the fluid is dispensed from the receptacle, and wherein the use of the boost function is measured and limited by the controller to prevent overdosing.

4. An infusion pump for administering controlled doses of a fluid, the pump comprising:
   a receptacle for storing the fluid, the receptacle having an outlet for dispensing the fluid;
   a plunger;
   a propulsion mechanism which urges the plunger in a direction to pressurize the fluid and dispense it through the outlet;
   a retaining member which acts on the plunger to control or prevent travel of the plunger; and
   a brake mechanism for preventing or inhibiting uncontrolled movement of the plunger, wherein the brake mechanism comprises a brake member for engaging with a wall of the receptacle;
   the retaining member operably connected to a motor via a worm and worm-wheel drive, in an arrangement wherein rotation of the worm causes the worm-wheel drive to rotate, and wherein the resulting rotation of the worm-wheel drive controls said travel of the plunger to dispense the fluid.

5. A pump according to claim 4, further comprising a piston located in the receptacle.

6. A pump according to claim 4, wherein the angle of teeth in the worm and worm-wheel drive is selected so that the drive is close to backdrive balance, whereby a small torque from the motor is sufficient to allow the worm-wheel to turn.

7. A pump according to claim 4, wherein the receptacle of the pump comprises a collapsible container.

8. A pump according to claim 4, wherein the brake member is a cruciform spring.

9. A pump according to claim 4, wherein during normal operation of the pump, the brake member adopts a retracted position and does not engage a wall of the receptacle.

10. A pump according to claim 9, wherein if the retaining member breaks, the brake member adopts a rest position and engages a wall of the receptacle.

11. A pump according to claim 4, wherein the brake member is adjustable between a rest configuration in which it will engage with a wall of the receptacle to prevent or inhibit relative movement between the plunger and the outlet, and a retracted configuration in which it does not engage with said wall, and wherein the brake member is held in the retracted configuration by the retaining member in normal operation but will be released to adopt the rest configuration if the retaining member fails.

12. A pump according to claim 11, wherein the arrangement is such that the propulsion mechanism urges the brake member to adopt the rest configuration if the retaining member fails.

13. A pump according to claim 4, wherein the brake member is arranged to cause the plunger to tilt if the retaining member fails, thereby causing jamming between the plunger and a wall of the receptacle.

14. A pump according to claim 4, wherein the propulsion mechanism comprises a compression spring.

15. A pump according to claim 14, in which the release of the spring is controlled by a capstan or winch.

16. A pump according to claim 15, wherein the capstan or winch is an axle of the worm-wheel of the worm and worm-wheel drive.

17. An infusion pump according to claim 4, further comprising a releasable hydraulic lock which when activated prevents fluid flow through the outlet and which when released permits fluid flow through the outlet.

18. A pump according to claim 4, wherein the motor is a stepper motor.

19. An infusion pump for administering controlled doses of a fluid, the pump comprising:
- a receptacle for storing the fluid, the receptacle having an outlet for dispensing the fluid;
- a plunger;
- a propulsion mechanism which urges the plunger in a direction to pressurize the fluid and dispense it through the outlet;
- a retaining member which acts on the plunger to control or prevent travel of the plunger, the retaining member operably connected to a stepper motor via a worm and worm-wheel drive; and
- a brake mechanism for inhibiting uncontrolled movement of the plunger, wherein the brake mechanism comprises a cruciform spring for engaging with a wall of the receptacle.

20. An infusion pump for administering controlled doses of a fluid, the pump comprising:
- a receptacle for storing the fluid, the receptacle having an outlet for dispensing the fluid;
- a plunger;
- a propulsion mechanism which urges the plunger in a direction to pressurize the fluid and dispense it through the outlet;
- a retaining member which acts on the plunger to control or prevent travel of the plunger, the retaining member operably connected to a stepper motor via a worm and worm-wheel drive; and
- a brake mechanism for inhibiting uncontrolled movement of the plunger, wherein the brake mechanism comprises a brake member for engaging with a wall of the receptacle, wherein during normal operation of the pump, the brake member adopts a retracted position and does not engage a wall of the receptacle, and if the retaining member breaks, the brake member adopts a rest position and engages a wall of the receptacle.

21. An infusion pump for administering controlled doses of a fluid, the pump comprising:
- a receptacle for storing the fluid, the receptacle having an outlet for dispensing the fluid;
- a plunger;
- a propulsion mechanism which urges the plunger in a direction to pressurize the fluid and dispense it through the outlet;
- a retaining member which acts on the plunger to control or prevent travel of the plunger, the retaining member operably connected to a stepper motor via a worm and worm-wheel drive; and
- a brake mechanism for inhibiting uncontrolled movement of the plunger, wherein the brake mechanism comprises a brake member for engaging with a wall of the receptacle, wherein the brake member is adjustable between a rest configuration in which it will engage with a wall of the receptacle to prevent or inhibit relative movement between the plunger and the outlet, and a retracted configuration in which it does not engage with said wall, and wherein the brake member is held in the retracted configuration by the retaining member in normal operation but will be released to adopt the rest configuration if the retaining member fails.

22. An infusion pump for administering controlled doses of a fluid, the pump comprising:
- a receptacle for storing the fluid, the receptacle having an outlet for dispensing the fluid;
- a plunger;
- a propulsion mechanism which urges the plunger in a direction to pressurize the fluid and dispense it through the outlet;
- a retaining member which acts on the plunger to control or prevent travel of the plunger, the retaining member operably connected to a stepper motor via a worm and worm-wheel drive; and
- a brake mechanism for inhibiting uncontrolled movement of the plunger, wherein the brake mechanism comprises a brake member for engaging with a wall of the receptacle, and wherein the brake member is arranged to cause the plunger to tilt if the retaining member fails, thereby causing jamming between the plunger and a wall of the receptacle.

* * * * *